United States Patent
Matsumoto et al.

(10) Patent No.: US 8,512,251 B2
(45) Date of Patent: Aug. 20, 2013

(54) ULTRASOUND TRANSDUCER AND ULTRASOUND DIAGNOSTIC APPARATUS

(75) Inventors: Kazuya Matsumoto, Nagano (JP); Katsuhiro Wakabayashi, Hachioji (JP); Jin Hiraoka, Sagamihara (JP); Kazuhisa Karaki, Shiojiri (JP); Mamoru Hasegawa, Nagano (JP); Satoshi Yoshida, Hachioji (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 0 days.

(21) Appl. No.: 13/614,168

(22) Filed: Sep. 13, 2012

(65) Prior Publication Data
US 2013/0018269 A1   Jan. 17, 2013

Related U.S. Application Data

(63) Continuation of application No. PCT/JP2011/076825, filed on Nov. 21, 2011.

(30) Foreign Application Priority Data

Mar. 24, 2011   (JP) ................................. 2011-066482

(51) Int. Cl.
*A61B 8/12* (2006.01)

(52) U.S. Cl.
USPC ............................ 600/459; 600/407; 600/437

(58) Field of Classification Search
USPC .......................................... 600/459; 73/606
See application file for complete search history.

(56) References Cited

U.S. PATENT DOCUMENTS

| | | |
|---|---|---|
| 2008/0089180 A1 | 4/2008 | Matsumoto et al. |
| 2008/0089181 A1 | 4/2008 | Adachi et al. |
| 2010/0198070 A1 | 8/2010 | Asafusa et al. |

FOREIGN PATENT DOCUMENTS

| | | |
|---|---|---|
| EP | 1 911 529 A1 | 4/2008 |
| EP | 2 030 698 A1 | 3/2009 |
| EP | 2 168 493 A1 | 3/2010 |
| JP | 2008-099036 | 4/2008 |
| JP | 2008-118631 | 5/2008 |
| JP | 2009-055474 | 3/2009 |
| JP | 2009-055475 | 3/2009 |
| WO | 2006/134580 A2 | 12/2006 |
| WO | WO 2009/008282 A1 | 1/2009 |

OTHER PUBLICATIONS

European Search Report dated Jun. 5, 2013 from corresponding European Patent Application No. 11 86 1763.8.

*Primary Examiner* — Unsu Jung
*Assistant Examiner* — Daniel Huntley
(74) *Attorney, Agent, or Firm* — Scully, Scott, Murphy & Presser, P.C.

(57) ABSTRACT

An ultrasound transducer includes a substrate and a lower electrode layer, a lower insulating layer, an upper insulating layer, and an upper electrode layer. The lower insulating layer and the upper insulating layer are arranged to be opposed to each other via an air gap section. The upper insulating layer and the lower insulating layer are different in a material and thickness and satisfy Equation 1 below. In Equation 1, $K1$ represents a relative dielectric constant of the lower insulating layer, $K2$ represents a relative dielectric constant of the upper insulating layer, $T1$ represents thickness of the lower insulating layer, $T2$ represents thickness of the upper insulating layer, $\rho1(x)$ represents a charge density distribution in the lower insulating layer, and $\rho2(y)$ represents a charge density distribution in the upper insulating layer.

$$\frac{1}{K1}\int_0^{T1} x \times \rho1(x)\,dx = \frac{1}{K2}\int_0^{T2} y \times \rho2(y)\,dy \quad \text{(Equation 1)}$$

8 Claims, 5 Drawing Sheets

ULTRASOUND TRANSDUCER AND ULTRASOUND DIAGNOSTIC APPARATUS

CROSS REFERENCE TO RELATED APPLICATION

This application is a continuation application of PCT/JP2011/076825 filed on Nov. 21, 2011 and claims benefit of Japanese Application No. 2011-066482 filed in Japan on Mar. 24, 2011, the entire contents of which are incorporated herein by this reference.

BACKGROUND OF THE INVENTION

1. Field of the Invention

The present invention relates to a capacitance type ultrasound transducer and an ultrasound diagnostic apparatus including the capacitance type ultrasound transducer.

2. Description of the Related Art

An ultrasound diagnostic method for irradiating an inside of a body with ultrasound, converting a state of the inside of the body into an image from an echo signal of the ultrasound, and performing diagnosis is widespread. As one of ultrasound diagnostic apparatuses used in the ultrasound diagnostic method, there is an ultrasound endoscope. In the ultrasound endoscope, an ultrasound transducer is disposed at a distal end of an insertion section introduced into the body. The ultrasound transducer has a function of converting an electric signal into an ultrasound and transmitting the ultrasound to the inside of the body and receiving the ultrasound reflected in the body and converting the ultrasound into an electric signal.

In the ultrasound transducer, a ceramic piezoelectric material, for example, PZT (lead zirconate titanate) is mainly used. On the other hand, as disclosed in Japanese Patent Application Laid-Open Publication No. 2009-55474, development of a capacitance type ultrasound transducer (Capacitive Micromachined Ultrasonic Transducer; hereinafter referred to as "c-MUT") manufactured using an MEMS (Micro Electro Mechanical Systems) technique is proceeding. The c-MUT applies a voltage between a fixed electrode and a movable electrode opposed via an insulating layer to vibrate the movable electrode and generate ultrasound. When a space between both the electrodes changes according to incident of ultrasound, the c-MUT detects a fluctuating capacitance value to detect the ultrasound.

SUMMARY OF THE INVENTION

An ultrasound transducer according to an aspect of the present invention includes a substrate and a lower electrode layer, a lower insulating layer, an upper insulating layer, and an upper electrode layer laminated in order on the substrate. The lower insulating layer and the upper insulating layer are arranged to be opposed to each other via an air gap section. The upper insulating film and the lower insulating film are different in at least one of a material and thickness and satisfy Equation 1 below.

$$\frac{1}{K1}\int_0^{T1} x \times \rho1(x)\,dx = \frac{1}{K2}\int_0^{T2} y \times \rho2(y)\,dy \quad \text{(Equation 1)}$$

where, K1 represents a relative dielectric constant of the lower insulating layer, K2 represents a relative dielectric constant of the upper insulating layer, T1 represents layer thickness of the lower insulating layer, T2 represents layer thickness of the upper insulating layer, $\rho1(x)$ represents a charge density distribution in the lower insulating layer (x represents a distance from the lower electrode layer), and $\rho2(y)$ represents a charge density distribution in the upper insulating layer (y represents a distance from the upper electrode layer).

An ultrasound diagnostic apparatus according to another aspect of the present invention includes the ultrasound transducer explained above.

DETAILED DESCRIPTION OF THE PREFERRED EMBODIMENTS

First Embodiment

An ultrasound transducer 2 according to a first embodiment of the present invention is explained below. Figures referred to below are schematic diagrams for explanation in which a scale and the like are different for each member.

Figure 1:
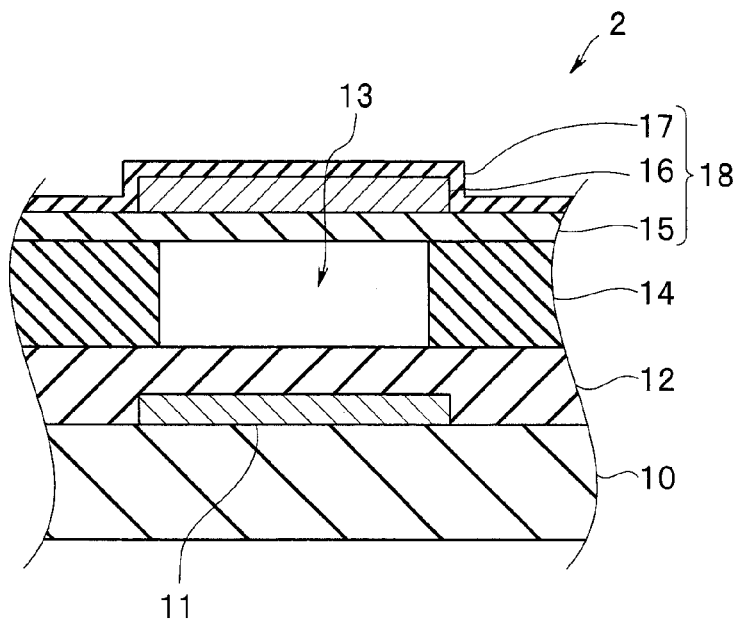
FIG. 1 is a diagram for explaining a sectional structure of an ultrasound transducer according to a first embodiment.

As shown in FIG. 1, an ultrasound transducer (hereinafter referred to as "transducer") 2 includes a substrate 10 and a lower electrode layer 11, a lower insulating layer 12, a gap layer 14, an upper insulating layer 15, and an upper electrode layer 16 laminated on the substrate 10 in order. The lower insulating layer 12 and the upper insulating layer 15 are arranged to be opposed to each other via an air gap section 13.

In explanation of the laminated structure, concerning a vertical relation of the respective layers, a direction away from a surface of the substrate 10 in a normal direction is represented as upper direction. For example, in FIG. 1, the upper electrode layer 16 is disposed above the lower electrode layer 11.

The transducer 2 of a capacitance type transmits and receives ultrasound according to a change in a distance between the upper electrode layer 16 and the lower electrode layer 11, i.e., vibration of a membrane 18 including the upper electrode layer 16 and the upper insulating layer 15. A protecting layer 17 may be arranged on the upper electrode layer 16 to form the membrane 18 including the protecting layer 17.

The air gap section 13 forms a space for the membrane 18 to vibrate. As explained below, a shape of the lower electrode layer 11, the air gap section 13, and the upper electrode layer 16 observed from above is not specifically limited. However, a circular shape or the like can be applied as the shape. A material of the substrate 10 is not specifically limited. However, examples of the material include a low-resistance silicon wafer having electric conductivity. An insulating layer (not shown in the figure) may be formed on the surface of the substrate 10.

Examples of the lower electrode layer 11 include MO (molybdenum), W (tungsten), Ti (titanium), Ta (tantalum), Al (aluminum), or Cu (copper). The lower electrode layer 11 may be a multilayer structure formed by laminating two or more kinds of conductive materials.

On the lower electrode layer 11, the lower insulating layer 12 is formed to cover the lower electrode layer 11. The lower insulating layer 12 is formed by, for example, a plasma CVD method. Examples of the lower insulating layer 12 include a silicon oxide layer, a silicon nitride layer, hafnium nitride (HfN), or hafnium oxynitride (HfON). However, as explained below, a material and layer thickness of the lower insulating layer 12 are determined in a relation with the upper insulating layer 15. The gap layer 14 that forms the air gap section 13 is formed on the lower insulating layer 12. A shape of the gap layer 14 is determined as appropriate according to a shape of the membrane.

The upper insulating layer 15 is formed on the gap layer 14. As the upper insulating layer 15, a material same as the material of the lower insulating layer 12 can be formed by a method same as a method of forming the lower insulating layer 12.

The upper insulating layer 15 and the lower insulating layer 12 are different in at least one of the material and the layer thickness. For example, when the upper insulating layer 15 and the lower insulating layer 12 are different in the material, the lower insulating layer 12 is a silicon oxide layer excellent in heat resistance having layer thickness of 500 nm and the upper insulating layer 15 is a silicon nitride layer having layer thickness of 500 nm. When the upper insulating layer 15 and the lower insulating layer 12 are different in the layer thickness, the lower insulating layer 12 is a silicon oxide layer having layer thickness of 150 nm and the upper insulating layer 15 is a silicon oxide layer having layer thickness of 500 nm thicker than the lower insulating layer 12. When the upper insulating layer 15 and the lower insulating layer 12 are different in the material and the layer thickness, the lower insulating layer 12 is a silicon oxide layer having layer thickness of 150 nm and the upper insulating layer 15 is a silicon nitride layer having layer thickness of 500 nm.

As the material of the upper insulating layer 15 and the lower insulating layer 12, an organic insulating material such as fluorine resin, polyimide, epoxy resin, or polyparaxylylene resin may be used.

Between the lower insulating layer 12 and the upper insulating layer 15, the air gap section 13 in an atmospheric pressure, pressurized, or depressurized state is formed by the gap layer 14. The depressurized state indicates a state in which pressure is lower than the atmospheric pressure and includes a so-called vacuum state as well. The air gap section 13 is formed in a substantially columnar shape and is provided substantially concentrically with the lower electrode layer 11 viewed from above.

The upper electrode layer 16 is formed on the upper insulating layer 15. The upper electrode layer 16 is provided substantially concentrically with the lower electrode layer 11 viewed from above, i.e., in a position opposed to the lower electrode layer 11. The upper electrode layer 16 is formed by, for example, forming an Al film with a sputtering method and patterning the Al film. The transducer 2 has a substantially circular shape viewed from above. However, the transducer 2 may be formed in, for example, a regular hexagonal shape or a rectangular shape.

A material forming the upper electrode layer 16 may be, for example, Cu, W, Ti, or Ta. The upper electrode layer 16 may have a multilayer structure formed by laminating two or more kinds of conductive materials.

The protecting layer 17 is formed on the upper electrode layer 16. The protecting layer 17 is, for example, a silicon nitride layer formed by the plasma CVD method. The protecting layer 17 may be a silicon oxide layer, hafnium nitride (HfN) layer, a hafnium oxynitride (HfON) layer, or the like.

Although not shown in the figure, a layer formed of resin such as polyparaxylylene resin or polyimide having water resistance, chemical resistance, and the like and excellent in biocompatibility and electric insulation may be formed on the protecting layer 17.

In general, the layer thicknesses and the like of the lower insulating layer 12 and the upper insulating layer 15 are determined on the basis of specifications such as a frequency of ultrasound to be transmitted and received, an output, ultrasound reception sensitivity, and dielectric strength voltage. However, the transducer 2 of this application further satisfies Equation 1 below.

$$\frac{1}{K1}\int_0^{T1} x \times \rho 1(x) dx = \frac{1}{K2}\int_0^{T2} y \times \rho 2(y) dy \qquad \text{(Equation 1)}$$

Figure 2:
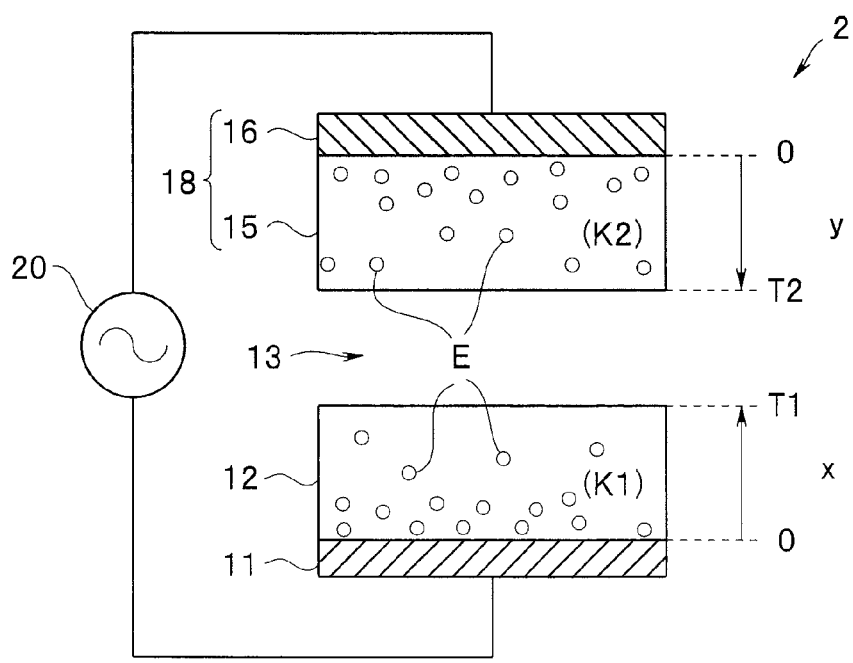
FIG. 2 is a diagram for explaining, for example, arrangement of opposed electrodes of the ultrasound transducer according to the first embodiment.
Figure 3:
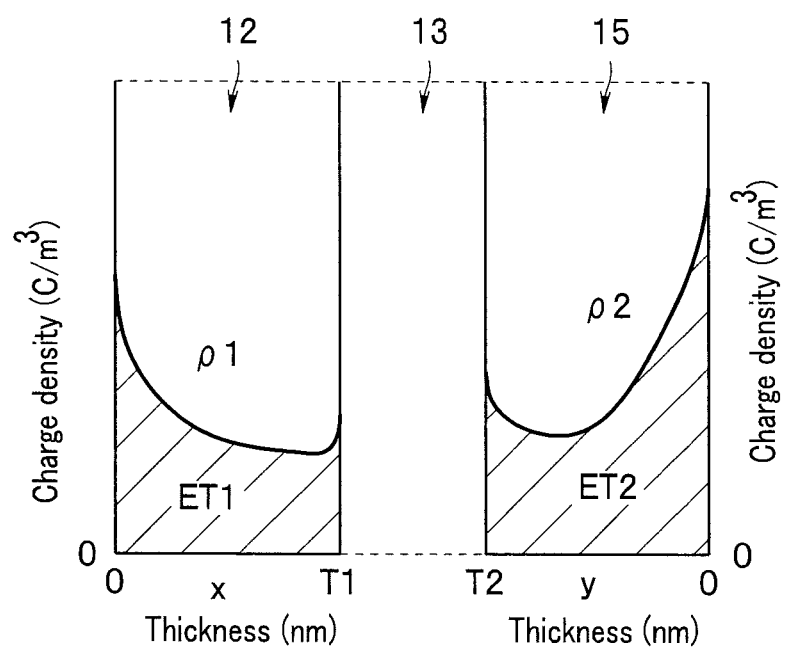
FIG. 3 is a diagram for explaining a charge distribution of an insulating layer of the ultrasound transducer according to the first embodiment.

As shown in FIGS. 2 and 3, K1 represents a relative dielectric constant of the lower insulating layer 12, K2 represents a relative dielectric constant of the upper insulating layer 15, T1 represents layer thickness of the lower insulating layer 12, T2 represents layer thickness of the upper insulating layer 15, $\rho 1(x)$ represents a charge density distribution in the lower insulating layer 12 (x represents a distance from the lower electrode layer), and $\rho 2(y)$ represents a charge density distribution in the upper insulating layer 15 (y represents a distance from the upper electrode layer). Amounts on both sides of Equation 1 are named as effective charge amounts (EE).

When a driving signal is applied to the ultrasound transducer, if an applied bias with which an electric current flows to an insulating film is used, charges are accumulated in the lower insulating layer and the upper insulating layer. In other words, values of $\rho 1$ and $\rho 2$ change. However, the values of $\rho 1$ and $\rho 2$ change while always keeping a proportional relation. An applied bias with which an electric current does not flow to the insulating film may be used or the values of $\rho 1$ and $\rho 2$ may be prevented from changing during driving of the ultrasound transducer. For example, a driving voltage may be reduced, the membrane may be hardened, a space between the upper insulating layer 15 and the lower insulating layer 12 may be increased, or an obstacle for contact prevention may be disposed in the cavity to prevent the upper insulating layer 15 and the lower insulating layer 12 from coming into contact with each other during the driving. Examples of a method of hardening the membrane include a method of adjusting thickness and a diameter of the insulating film.

An example of charge distributions in the insulating layers is shown in FIG. 3. In the example shown in FIG. 3, a relatively large number of charges E are present in regions near the electrode layers and density distributions $\rho$ are different in the upper insulating layer 15 and the lower insulating layer 12.

The inventor found as a result of extensive studies that what affects characteristics of the transducer 2 is not a total charge amount ET, i.e., a total charge amount in a layer and that a charge density distribution and the like are important factors.

An integrated value of a charge density distribution indicated by hatching in FIG. 3 is equivalent to the total charge amount ET. For example, a total charge amount ET1 of the lower insulating layer 12 is indicated by Equation 2 below.

$$ET1 = \int_0^{T1} \rho(x)dx \quad \text{(Equation 2)}$$

However, even if the total charge amount ET1 of the lower insulating layer 12 and a total charge amount ET2 of the upper insulating layer 15 were the same, the characteristics of the transducer 2 did not stabilize.

This is because the charges E in positions close to the electrode layers and the charges E in positions far from the electrode layers had different influences on the characteristics of the transducer 2. Therefore, thicknesses of the insulating layers related to the characteristics of the transducer. Further, relative dielectric constants K of the electrode layers also contributed to the characteristics of the transducer.

It was confirmed that a product of distances from the electrode layers, in other words, positions (x, y) in a layer thickness direction of the insulating layers and the charges E present in the positions and the relative dielectric constants K of the respective electrode layers affected the characteristics of the transducer 2. For example, even if the number of electrons (charges) present near the electrode layers is large, influences on potential are small. Equation 1 that takes into account the amounts of charges, the positions, and the dielectric constants indicates the effective charge amount EE, which is an accumulated charge amounts that affect the potential.

In other words, when Equation 1 is satisfied, since the influences of the charges on the potential are equivalent to each other, the characteristics of the transducer 2 stabilize.

For example, when silicon oxide ($SiO_2$) having layer thickness of 200 nm was used as the lower insulating layer 12 and K1=4.0, a total charge amount ET1 indicated by Equation 2 was 8E-8 C/cm$^2$. On the other hand, when the upper insulating layer 15 was silicon nitride ($Si_3N_4$) having layer thickness of 500 nm and K2=8.0, a total charge amount ET2 indicated by Equation 2 was 6.4E-8 C/cm$^2$.

In short, the total charge amount ET1 of the lower insulating layer 12 and the total charge amount ET2 of the upper insulating layer 15 are different.

However, in this case, an effective charge amount EE1 on the left side of Equation 1 was 4E-13 C/cm and an effective charge amount EE2 on the right side was 4E-13 C/cm. "E-13" indicates $10^{-13}$.

Specifically, since Equation 1 was satisfied, the characteristics of the transducer 2 stabilized. Incidentally, because of presence of these effective charge amounts, both potential differences from the electrodes to a surface of the insulating film are 4.5 V.

For measurement of a charge density distribution, a publicly-known measuring apparatus can be used. Further, it is also possible to measure surface potential while removing a surface layer little by little. For the removal of the surface layer, a polishing method or an etching method can be used. For example, a silicon oxide layer is gradually etched by a buffered fluoric acid solution at speed of 100 nm/minute.

As explained above, the characteristics of the ultrasound transducer 2 according to the embodiment are stable because there is no influence of charge accumulation on the insulating layers.

To adjust the effective charge amount EE to satisfy Equation 1, it is desirable from viewpoints of easiness of a manufacturing method and easiness of control to change the layer thicknesses of the lower insulating layer 12 and the upper insulating layer 15.

Second Embodiment

Next, an ultrasound endoscope 3, which is an ultrasound diagnostic apparatus, according to a second embodiment of the present invention is explained. An ultrasound transducer 2A included in an ultrasound transmitting and receiving section 30 of the ultrasound endoscope 3 is the same as the ultrasound transducer 2 according to the first embodiment. Therefore, explanation of the ultrasound transducer 2A is omitted.

Figure 4:
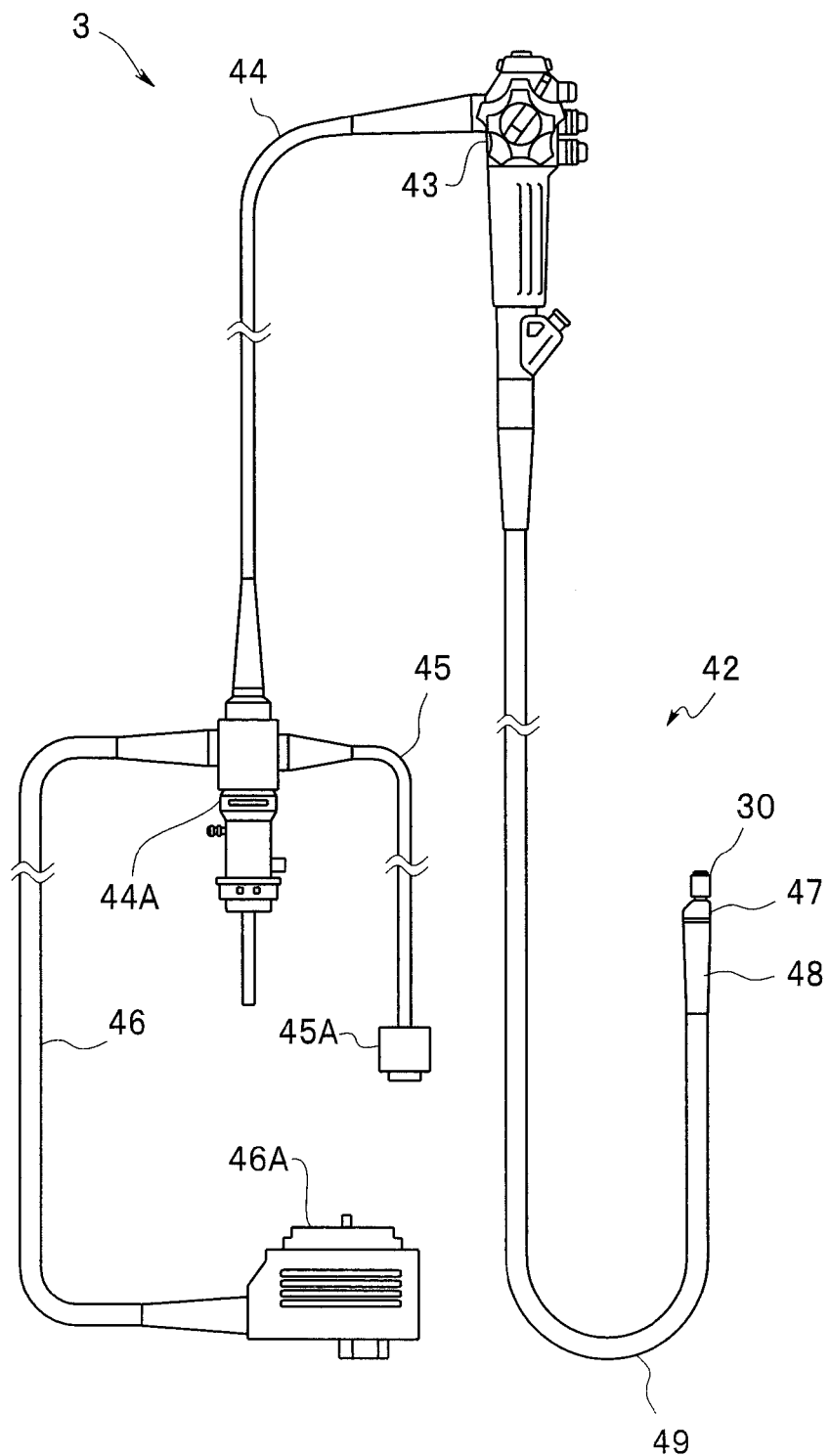
FIG. 4 is a diagram for explaining an ultrasound endoscope according to a second embodiment.

As shown in FIG. 4, the ultrasound endoscope 3 includes an insertion section 42, an operation section 43, and a universal cord 44. An endoscope connector 44A is provided in a proximal end portion of the universal cord 44. An electric cable 45 connected to a camera control unit (not shown in the figure) via an electric connector 45A and an ultrasound cable 46 connected to an ultrasound observation apparatus (not shown in the figure) via an ultrasound connector 46A extend from the endoscope connector 44A.

In the insertion section 42, a rigid portion 47, a bending portion 48, and a flexible tube portion 49 are continuously provided.

On a distal end side of the rigid portion 47, the ultrasound transmitting and receiving section 30 including the transducer 2 for transmitting and receiving ultrasound is provided.

Figure 5:
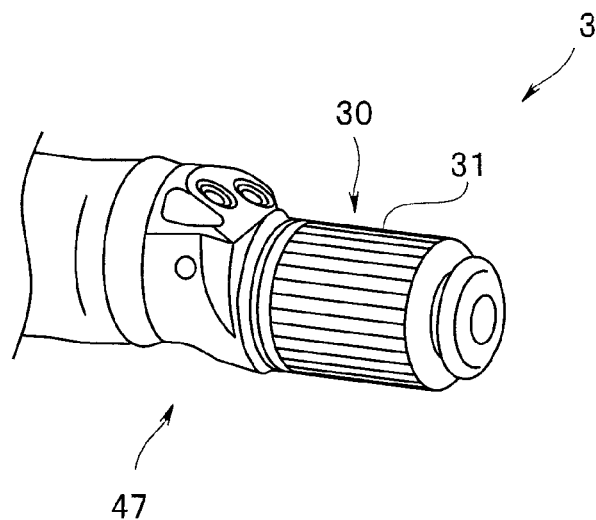
FIG. 5 is a diagram for explaining a distal end portion of the ultrasound endoscope according to the second embodiment.
Figure 6:
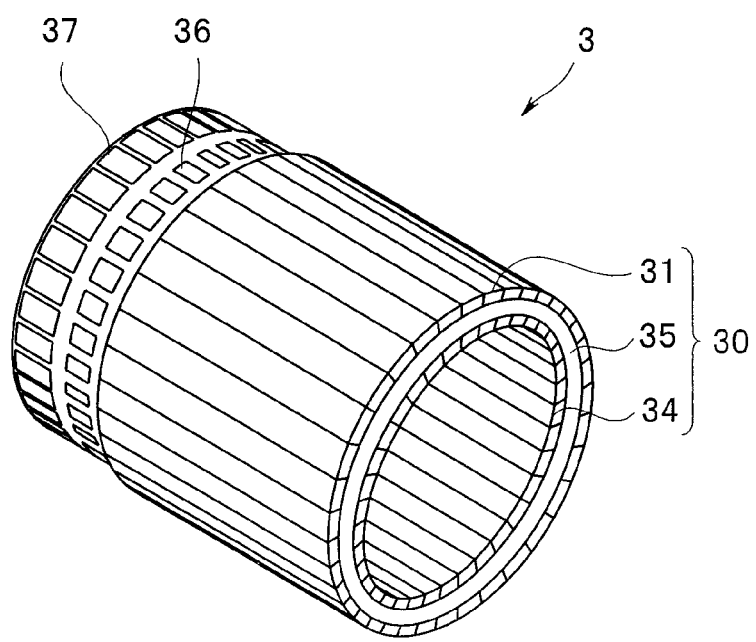
FIG. 6 is a diagram for explaining an ultrasound transmitting and receiving section of the ultrasound endoscope according to the second embodiment.

As shown in FIGS. 5 and 6, the ultrasound transmitting and receiving section 30 includes a transducer array 31, driving circuits 34, and an FPC 35. The FPC 35 is a flexible wiring board having flexibility and having mounting surfaces formed on both surfaces thereof. The FPC 35 is wound around in a substantially cylindrical shape with an axis substantially parallel to an insertion axis of the rigid portion 47 set as a center axis.

On an outer circumferential surface of the cylindrical FPC 35, the two-dimensional ultrasound transducer array (hereinafter referred to as "transducer array") 31 is provided. The transducer array 31 includes one hundred twenty-eight transducer units 32 arrayed on the outer circumferential surface of the FPC 35 in a circumferential direction. The transducer units 32 have a substantially rectangular shape viewed from a normal direction of the outer circumferential surface of the FPC 35. The transducer units 32 are arrayed at an equal interval on the outer circumferential surface of the cylindrical FPC 35 with a latitudinal direction set as a circumferential direction.

Figure 7:
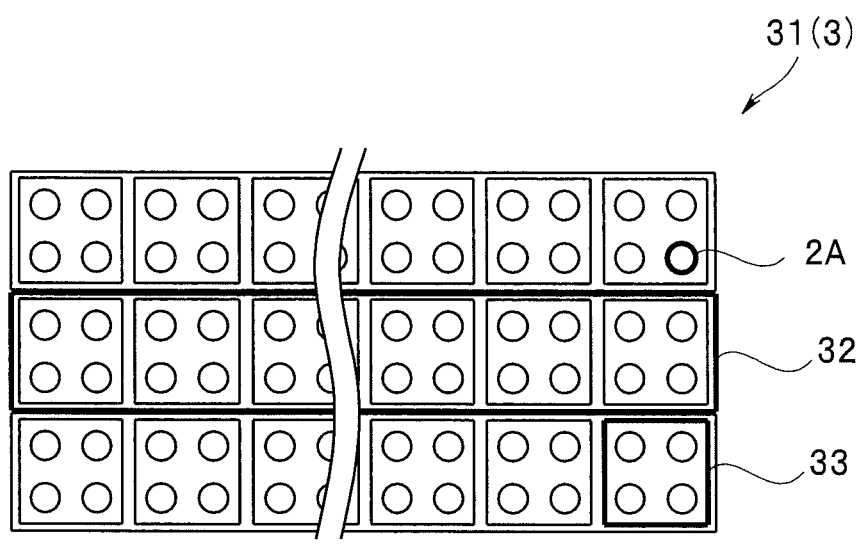
FIG. 7 is a diagram for explaining an ultrasound transducer of the ultrasound endoscope according to the second embodiment.

As shown in FIG. 7, each of the transducer units 32 is configured by arraying sixty-four transducer elements 33. The transducer elements 33 have a substantially square shape viewed from the normal direction of the outer circumferential surface of the FPC 35. The transducer units 32 are one-dimensionally arrayed in a longitudinal direction of the transducer unit.

Further, each of the transducer elements 33 includes four ultrasound transducers 2A. The four transducers 2 are connected in parallel and transmit ultrasound of the same phase simultaneously with input of a driving signal.

On an inner circumferential surface of the FPC 35, i.e., on the mounting surface on an opposite side of the mounting surface on which the respective transducer arrays 31 are mounted, the driving circuits 34 for the transducer array 31 are mounted. The driving circuits 34 are electrically connected to plural signal electrodes 36 and plural ground electrodes 37 formed on the outer circumferential surface of the cylindrical FPC 35.

The signal electrodes 36 and the ground electrodes 37 are inserted through the ultrasound cable 46 and connected to the ultrasound observation apparatus via the ultrasound connector 46A.

The ultrasound transmitting and receiving section 30 simultaneously or alternately performs, with the transducer array 31, electronic radial scanning for radially transmitting and receiving ultrasound on a plane substantially orthogonal to the insertion axis of the rigid portion 47 and electronic sector scanning for radially transmitting and receiving ultrasound on a plane including the insertion axis of the rigid portion 47. In other words, the ultrasound endoscope 3 can perform three-dimensional ultrasound scanning.

The ultrasound endoscope 3 includes the ultrasound transducer 2A that is not affected by accumulation in the insulating layers. Therefore, the characteristics of the ultrasound endoscope 3 are stable. It is possible to obtain a high-quality and satisfactory ultrasound diagnostic image.

The ultrasound endoscope 3 performs the electronic radial scanning and the electronic sector scanning. However, a scanning system is not limited to these and may be linear scanning, convex scanning, or mechanical scanning. An ultrasound transmitting and receiving section in which plural transducer elements are one-dimensionally arrayed may be adopted.

The ultrasound diagnostic apparatus may be an ultrasound probe or the like inserted through a treatment instrument through-hole of an endoscope and introduced into a body.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasound transducer comprising: a substrate; and a lower electrode layer, a lower insulating layer, an upper insulating layer, and an upper electrode layer laminated in order on the substrate, wherein
the lower insulating layer and the upper insulating layer are arranged to be opposed to each other via an air gap section, are different in at least one of a material and thickness, and satisfy Equation 1 below:

$$\frac{1}{K1}\int_0^{T1} x \times \rho 1(x)\,dx = \frac{1}{K2}\int_0^{T2} y \times \rho 2(y)\,dy$$

where, K1 represents a relative dielectric constant of the lower insulating layer, K2 represents a relative dielectric constant of the upper insulating layer, T1 represents layer thickness of the lower insulating layer, T2 represents layer thickness of the upper insulating layer, $\rho 1(x)$ represents a charge density distribution in the lower insulating layer, x represents a distance from the lower electrode layer, $\rho 2(y)$ represents a charge density distribution in the upper insulating layer, and y represents a distance from the upper electrode layer.

2. The ultrasound transducer according to claim 1, wherein the layer thicknesses of the lower insulating layer and the upper insulating layer made of a same material are different.

3. The ultrasound transducer according to claim 1, wherein the lower insulating layer and the upper insulating layer are different in the material and the layer thickness.

4. The ultrasound transducer according to claim 1, wherein the lower insulating layer and the upper insulating layer do not come into contact with each other during driving, and the $\rho 1(x)$ and the $\rho 2(x)$ do not change even if a driving signal is applied to the lower electrode layer and the upper electrode layer.

5. An ultrasound diagnostic apparatus comprising an ultrasound transducer including: a substrate; and a lower electrode layer, a lower insulating layer, an upper insulating layer, and an upper electrode layer laminated in order on the substrate, wherein
the lower insulating layer and the upper insulating layer are arranged to be opposed to each other via an air gap section, are different in at least one of a material and thickness, and satisfy Equation 1 below:

$$\frac{1}{K1}\int_0^{T1} x \times \rho 1(x)\,dx = \frac{1}{K2}\int_0^{T2} y \times \rho 2(y)\,dy$$

where, K1 represents a relative dielectric constant of the lower insulating layer, K2 represents a relative dielectric constant of the upper insulating layer, T1 represents layer thickness of the lower insulating layer, T2 represents layer thickness of the upper insulating layer, $\rho 1(x)$ represents a charge density distribution in the lower insulating layer, x represents a distance from the lower electrode layer, $\rho 2(y)$ represents a charge density distribution in the upper insulating layer, and y represents a distance from the upper electrode layer.

6. The ultrasound diagnostic apparatus according to claim 5, wherein, in the ultrasound transducer, the layer thicknesses of the lower insulating layer and the upper insulating layer made of a same material are different.

7. The ultrasound diagnostic apparatus according to claim 5, wherein, in the ultrasound transducer, the lower insulating layer and the upper insulating layer are different in the material and the layer thickness.

8. The ultrasound diagnostic apparatus according to claim 5, wherein, in the ultrasound transducer, the lower insulating layer and the upper insulating layer do not come into contact with each other during driving, and the $\rho 1(x)$ and the $\rho 2(x)$ do not change even if a driving signal is applied to the lower electrode layer and the upper electrode layer.

* * * * *